United States Patent [19]

Sauer et al.

[11] Patent Number: 4,863,929
[45] Date of Patent: * Sep. 5, 1989

[54] 12- AND 13-SUBSTITUTED ERGOLINE DERIVATIVES HAVING ALPHA$_2$-RECEPTOR-BLOCKING EFFECT

[75] Inventors: Gerhard Sauer; Josef Heindl; Gertrud Schroeder; Helmut Wachtel, all of Berlin, Fed. Rep. of Germany

[73] Assignee: Schering Aktiengesellschaft, Berlin and Bergkamen, Fed. Rep. of Germany

[*] Notice: The portion of the term of this patent subsequent to Apr. 26, 2005 has been disclaimed.

[21] Appl. No.: 909,838

[22] Filed: Sep. 19, 1986

[30] Foreign Application Priority Data

Sep. 19, 1985 [DE] Fed. Rep. of Germany ....... 3533672

[51] Int. Cl.$^4$ .................... A61K 31/48; C07D 457/12
[52] U.S. Cl. ...................... 514/288; 546/14; 546/68
[58] Field of Search .............. 546/14, 68; 514/288

[56] References Cited

U.S. PATENT DOCUMENTS

| | | | |
|---|---|---|---|
| 4,500,712 | 2/1985 | Bernardi et al. | 546/67 |
| 4,740,509 | 4/1988 | Sauer et al. | 546/68 |

FOREIGN PATENT DOCUMENTS

| | | | |
|---|---|---|---|
| 0021206 | 1/1981 | European Pat. Off. | |
| 48695 | 3/1982 | European Pat. Off. | |
| 56358 | 7/1982 | European Pat. Off. | |
| 0082808 | 6/1983 | European Pat. Off. | |
| 118848 | 9/1984 | European Pat. Off. | 546/68 |
| 0160842 | 11/1986 | European Pat. Off. | |
| 3533672 | 3/1987 | Fed. Rep. of Germany | 546/68 |
| 3533675 | 3/1987 | Fed. Rep. of Germany | |
| 8202892 | 9/1982 | World Int. Prop. O. | |

*Primary Examiner*—Cecilia Shen
*Attorney, Agent, or Firm*—Millen, White & Zelano

[57] ABSTRACT

Novel 12- and 13-substituted ergoline derivatives are suitable, e.g., as psychopharmaceuticals and for hypertension therapy.

19 Claims, No Drawings

12- AND 13-SUBSTITUTED ERGOLINE DERIVATIVES HAVING ALPHA$_2$-RECEPTOR-BLOCKING EFFECT

The invention relates to 12- and 13-substituted ergoline derivatives of Formula I, to their production, and to their use as medicines.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been attained by providing the compound of this invention of the Formula I (I)

wherein
$R^1$ is in the 12- or 13- position,
$R^1$ is OR', SH—, SR$^5$—, SOR$^5$, $$-\underset{X}{\overset{\parallel}{C}}-R^6,$$

—CR$^8$R$^9$R$^{10}$, SO$_2$CF$_3$—, Si(CH$_3$)$_3$—, CN, Cl or I,
R' is H, lower alkyl, or acyl,
R$^5$ is lower alkyl, aryl, or aralkyl,
X is O or S,
R$^6$ is H, CF$_3$, aryl, lower alkyl, an amino group optionally substituted by lower alkyl, or OR$^7$,
R$^7$ is hydrogen or lower alkyl,
R$^8$ is H, OH, O-acyl, O-lower alkyl, aryl, lower alkyl, or an amino group optionally substituted by lower alkyl,
R$^9$ and R$^{10}$, being identical or different, are each H, lower alkyl or aryl,
R$^2$ is lower alkyl,
R$^3$ is NH—CO—NEt$_2$ or NH—CS—NEt$^2$,
C$_2$=C$_{10}$ and C$_2$=C$_3$ are each independently a CC-single or a C=C double bond, and
the hydrogen atom in the 10-position is in the alpha-configuration if C$_9$=C$_{10}$ is a CC-single bond, and the hydrogen atom in the 3-position is in the alpha- or beta-configuration if C$_2$=C$_3$ is a CC-single bond,
as well as the acid addition salts thereof.

Lower alkyl residues throughout include, e.g., those of up to 6 carbon atoms. C$_1$–C$_4$-alkyls are preferred. For example, included are methyl, ethyl, isopropyl, n-propyl, n-butyl, isobutyl, tert-butyl, a pentyl, a hexyl etc.

Aryl groups are typically of 6–10 C-atoms. Aralkyl groups generally are of 1–6 C-atoms in the alkyl group and 6–10 C atoms in the aryl group. Preferred aralkyl residues are those of up to 2 carbon atoms in the alkyl residue, for example, benzyl and phenethyl. Aryl residues and the aralkyl residues, can be optionally substituted, for example, by lower alkyl, lower alkoxy (C$_1$–C$_6$), or halogen (e.g., F, Cl, Br, I).

The acyl residues are generally derived from aliphatic carboxylic acids of 1–6, preferably of 2–5 carbon atoms, e.g., acetic acid, propionic acid, butyric acid, caproic acid, and tri-methylacetic acid.

The amino group, is optionally mono- or disubstituted by lower alkyl.

The salts of this invention according to Formula I are acid addition salts and are derived from conventionally employed acids making them pharmacologically acceptable. Such acids are, for example,.inorganic acids, such as, for example, hydrochloric acid, nitric acid, phosphoric acid, sulfuric acid, hydrobromic acid, hydriodic acid, nitrous acid or phosphorous acid, hydriodic acid, nitrous acid or phosphorous acid, or organic acids, such as, for example, aliphatic mono- or dicarboxylic acids, phenyl-substituted alkanecarboxylic acids, hydroxyalkanecarboxylic acids or alkenedicarboxylic acids, aromatic acids or aliphatic or aromatic sulfonic acids. Physiologically acceptable salts of these acids are, therefor, e.g. the sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propiolate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, beta-hydroxybutyrate, glycolate, malate, tartrate, methanesulfonate, propanesulfonite, naphthalene-1-sulfonate or naphthalene-2-sulfonate.

As compared with conventional ergolines unsubstituted in the 12 and 13-position, for example, trans-dihydrolisuride, the compounds according to this invention possess a stronger, or at least equally strong, central alpha2-receptor-blocking effect with weaker, or a lack of antidopaminergic effects. This profile of activity renders the compounds valuable substances for the treatment of psychic disorders of the depressive array of symptoms. Thus the compounds can be used as general antidepressants to treat symptoms including endogenous depression, agitated or restrained depression, idiophathic depression, lack or loss of drive, of interest, of thinking, of energy, of hope, etc., or a feeling of emptiness. They also are useful to treat excitability, subjective feelings of unrest, dysphoria or anxiety.

The antidepressive effect of the compounds according to this invention is based on central alpha$^2$-receptor blockage causing increased release of noradrenalin in the brain and moreover showing the antidepressive activity as a consequence thereof. Central alpha$^2$-receptor blockage was demonstrated in an interaction test with the alpha$^2$-receptor against clonidine on mice after one-time i.p. pretreatment (parameter: relief of hypothermia caused by clonidine 0.1 mg/kg i.p). Male NMRI mice were pre-treated with various doses of 1,1-diethyl-(6-methyl-8 alpha-ergolinyl)urea (TDHL) or, with 13-substituted ergolinylureas which per se do not affect thermoregulation of the test animals, or with carrier medium. Thirty minutes later, all animals received clonidine 0.1 mg/kg i.p. Rectal temperature was measured with the aid of a thermal probe 60 minutes after the test compound or the carrier medium (=30 minutes after clonidine). While the mice pretreated with carrier medium showed hypothermia, the effect of clonidine of lowering body temperature was cancelled out in dependence on the dose in animals pretreated with TDHL and 13-substituted ergolinylureas. As can be seen from Table 1, the clonidine-antagonistic effect

TABLE 1

Antagonistic Effect on Hypothermia in Mice Caused by Clonidine (0.1 mg/kg p.i.) of the Pretreatment (30 min. i.p.) with Various Doses of 13-Substituted Ergolinylureas. Rectal Temperature of the Test Animals Was Measured 30 min. after Clonidine (=60 min. after Test Compound)

| Compound | n | Control | \multicolumn{7}{c}{Rectal Temperature [°C](Average Value ± S.E.M.) Test Compound Dose [mg/kg]} |
|---|---|---|---|---|---|---|---|---|---|
|  |  |  | 0.05 | 0.1 | 0.2 | 0.39 | 0.78 | 1.56 | 3.13 |
| TDHL | 8 | 33.1 ± 0.2 | — | — | — | 33.6 ± 0.2 | 33.7 ± 0.3 | 34.1 ± 0.2 | 34.7 ± 0.3 |
| 13-SCH$_3$—TDHL | 8 | 33.5 ± 0.2 | — | 33.9 ± 0.2 | 34.0 ± 0.3 | 34.4 ± 0.2 | 35.1 ± 0.3 | 35.5 ± 0.2 | 35.6 ± 0.3 |

*(x: $p < 0.05$, xx: $p < 0.01$ vs. Control; Variance Analysis/Dunnett Test)

TABLE 2

Antagonistic Effect on Hypothermia in Mice Caused by Apomorphine (5 mg/kg i.p.) of the Pretreatment (30 min. i.p.) with Various Doses of 13-Substituted Ergoline Ureas. Rectal Temperature of the Test Animals Was Measured 30 min. after Apomorphine (=60 min. after Test Compound)

| Compound | n | Control | \multicolumn{7}{c}{Rectal Temperature [°C] (Average Value ± S.E.M.) Test Compound dose [mg/kg]} |
|---|---|---|---|---|---|---|---|---|---|
|  |  |  | 0.05 | 0.1 | 0.2 | 0.39 | 0.78 | 1.56 | 3.13 | 6.25 |
| TDHL | 8 | 32.5 ± 0.4 | — | — | — | — | 33.9 ± 0.5 | 33.8 ± 0.4 | 35.1 ± 0.5 | 35.5 ± 0 |
| 13-SCH$_3$—TDHL | 8 | 32.3 ± 0.3 | — | 32.5 ± 0.3 | 31.5 ± 0.1 | 31.9 ± 0.5 | 32.7 ± 0.6 | 33.3 ± 0.4 | 32.8 ± 0.5 | — |

*(x: $p < 0.05$, xx: $p < 0.01$ vs. Control; Variance Analysis/Dunnett Test)

after 13-SCH$_3$-TDHL in a dosage of 0.78 mg/kg was statistically significant.

Central dopamine receptor blockage was demonstrated in an interaction test with the dopamine receptor agonist apomorphine on mice after a one-time i.p. pretreatment. (Parameter: relief of hypothermia caused by apomorphine 5 mg/kg i.p.) The further procedure was like the method described in central alpha -receptor blockage.

As can be seen from Table 2, the apomorphine-antagonistic effect was highly significant statistically after TDHL administration in a dosage of 3.13 mg/kg. In doses of 0.1–3.13 mg/kg, 13-SCH$_3$-TDHL had no apomorphine-antagonistic effect.

Based on these findings, the compounds of this invention can thus be utilized as adjunct to neuroleptics for the treatment of psychoses of the schizophrenic array of symptoms especially with negative clinical symptoms or as antidepressants. Furthermore, the compounds of this invention show blood-pressure lowering effect and therefore are useful as medicines for the therapy of hypertension.

In animal-pharmacological assays, 1,1-diethyl-(13-hydroxy-6-methyl-8 alpha-ergolinyl) urea (13-OH-TDHL), for example, showed a dose-dependent lowering of the blood pressure in spontaneously hypertensive rats, prepared according to a method modified in accordance with Weeks (Weeks, J. R., "Routine Direct Measurement of Arterial Pressure in Anaesthetized Rats", Proc. S. Exp. Biol. Med., 104: 646–648, 1960).

In order to investigate antihypertensive activity and its dependence on the dose, the following pharmacological tests were carried out:

In male SH-rats, weighing about 300 g, the medium arterial blood pressure and cardiac frequency were determined by means of an implanted aorta catheter. The test compound was administered intravenously in a bolus via catheter placed in the jugular vein in the dosages of 0.01 mg/kg, 0.1 mg/kg, and 1.0 mg/kg of body weight, after having been dissolved in DMSO and filled up with distilled water to the volume to be administered. The maximum lowering of blood pressure after administering 1.0 mg/kg body weight is, using for example 13-OH-TDHL, 35% of the starting value; at this dose, the antihypertensive activity persists up to the end of the test after 120 minutes. Cardiac frequency is lowered by maximally 30% with a dose of 1 mg/kg body weight.

The compounds of this invention are prepared according to methods known per se, by reacting a 12- or 13-Brergoline derivative of general Formula II

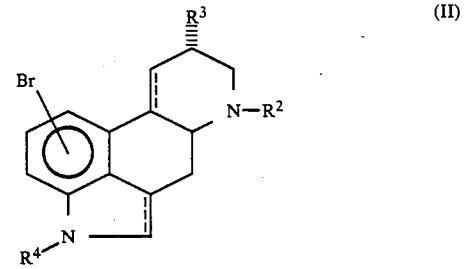

wherein
R$^2$, R$^3$ and CC have the meanings given above and
R$^4$ is hydrogen or a blocking group, with a lithium organyl, and reacting the thus-obtained 12- or 13-Li-ergoline derivative of general Formula III

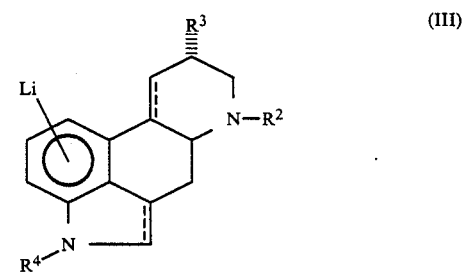

wherein $R^4$, $R^2$, $R^3$ and CC have the above-indicated meanings, with an electrophilic reagent.

If desired, subsequently, an OH group is alkylated or acylated, a carboxy function is esterified, an aldehyde function is reduced, a carboxylic acid amide is converted into a nitrile, a sulfur atom is oxidized, and/or a urea is converted into a thiourea, and optionally converted, with an acid, into the physiologically compatible acid addition salt.

For producing the compounds of general Formula III, all conventional lithium organyls can be utilized, lithium alkyls and lithium phenyl being preferred. An especially preferred alkyllithium compound is tert-butyllithium, of which 1–10 equivalents are employed. The reaction is conducted in an aprotic solvent, such as ether or a hydrocarbon, for example in tetrahydrofuran, dioxane, diethyl ether, toluene, hexane, etc. The addition of a stoichiometric amount of tetramethylethylenediamine, based on the alkyllithium compound, has proven to be advantageous.

$R^4$ can represent a customarily utilized blocking group, such as, for example, an acyl or silyl residue, the trialkylsilyl residue, especially the tert-butyldimethylsilyl group, is preferred.

The bromine-lithium exchange is performed at temperatures of 20° C. to −110° C.; in the presence of a blocking group, temperatures of −70° to −110° C. are preferred, and, without a blocking group, the preferred temperatures are 20° C. to −70° C. In order to avoid secondary reactions, the proton on the urea can be removed prior to bromine-lithium exchange by means of the usual methods, such as, for example, by adding diisopropylamide or lithium bis(trimethylsilyl)amide in stoichiometric quantities. The reaction is finished after about 5 minutes to 2 hours and is suitably conducted under an inert gas, e.g. argon or nitrogen.

The resultant lithium-ergoline derivative of general Formula III is reacted, without being worked up any further, with the electrophilic reagent in the aprotic solvent.

Suitable electrophilic reagents are, for example: thiosulfonic acid S-esters, such as, for example, methanethiosulfonic acid S-methyl ester, toluenethiosulfonic acid S-ethyl ester, toluenethiosulfonic acid S-n-propyl ester; disulfides, such as, for example, dibenzyl disulfide, diphenyl disulfide, tetraisopropylthiuram disulfide; isocyanates and isothiocyanates, such as, for example, trimethylsilyl isocyanate, methyl isothiocyanate; formamides, such as, for example, dimethylformamdie; aldehydes, such as, for example, benzaldehyde; iminium compounds, such as, for example, N,N-dimethyl methylene iminium iodide, N,N-dimethylmethylene iminium chloride; halogenides, such as, for example, alkyl halogenides, e.g. methyl iodide, isopropyl iodide, alkyl bromide, halogenated silanes, e.g., trimethylchlorosilane, acid chlorides, e.g. acetyl chloride, halogenating agents, e.g., N-chlorosuccinimide, N-iodosuccinimide, and halogen, for example iodine; anhydrides, such as, for example, trifluoroacetic anhydride, trifluoromethanesulfonic anhydride; boric acid trimethyl ester; nitrobenzene; $CO_2$, and others to prepare the full scope of $R^1$ groups, with further reactions where necessary.

If the reactant is a gas under normal conditions, then this compound is introduced in the gaseous phase or made to react in the solid form, such as, for example, as solid carbon dioxide.

Electrophilic substitution is carried out at low temperatures (0° C. to −90° C.) and thereafter the reaction mixture is stirred optionally at room temperature for about 2 hours. If present, the blocking group $R^4$ can be split off at room temperature according to the conventional methods by treatment with acids, such as dilute mineral acid, trifluoroacetic acid, or inorganic bases, such as KOH, NaOH, or fluoride, such as tetrabutylammonium fluoride in inert solvents, e.g., water, alcohols, hydrocarbons, and others. When using the trialkyl ester of boric acid as the electrophilic reagent, a solution of $H_2O_2$ must be added to introduce the OH-group.

If desired, the substituents in the 12- and 13-positions can subsequently be reacted by conventional methods. For example, the OH-groups can be alkylated, e.g. with an alkyl halogenide in solvents such as DMF, DMSO, acetone, in the presence of bases, such as NaH, $K_2CO_3$ at room temperature or elevated temperature, or acylated, e.g., with acid chlorides or acid anhydrides in the presence of amines of pyridine at room temperature. Carboxylic acid amides can be converted into nitriles, for example by reaction with phosphorus oxychloride without a solvent or in an aprotic solvent, such as ether, methylene chloride, at room temperature or elevated temperature. When $R^1$ is an alkyl mercaptan group, the latter can be oxidized to the sulfinyl group, for example by oxidizing to the sulfoxide with sodium metaperiodate in an inert solvent, such as acetonitrile, dioxane, THF, at room temperature or elevated temperature.

When $R^1$ is an aldehyde group, the latter can be reduced to the corresponding alcohol, for example by performing reduction with lithium aluminum hydride in an aprotic solvent, such as ether, for example THF, diethyl ether, at room temperature.

If $R^1$ is a carboxylic acid group, the latter can be esterified by dissolving in an alcohol, such as, for example, methanol or ethanol, in the presence of an acid, such as hydrogen chloride or p-toluenesulfonic acid.

Conversion of the 8 alpha-urea derivatives into the corresponding thiones takes place by reaction with phosphorus oxychloride and subsequent reaction with potassium xanthate. The reaction is performed at low temperatures with intermediate raising of the temperature, in inert solvents, such as ethers.

For the formation of salts, the compounds of Formula I can be dissolved in a small amount of methanol or methylene chloride and combined with a concentrated solution of the desired acid in methanol at room temperature.

The starting materials of Formula II are preparable from known or readily preparable starting materials by conventional reactions. See, e.g., copending application Ser. No. 909,837, filed Sept. 19, 1986, U.S. Pat. No. 4,740,509 (equivalent to DE-OS 3533675) which disclosure is incorporated by reference herein.

For using the compounds of this invention as medicinal agents, they can be brought into the form of a pharmaceutical preparation containing, in addition to the active agent, pharmaceutical, organic or inorganic, inert excipients suitable for enteral or parenteral administration, such as, for example, water, gelatin, gum arabic, lactose, amylose, magnesium stearate, talc, vegetable oils, polyalkylene glycols, etc. The pharmaceutical preparations can be present in solid form, e.g. as tablets, dragees, suppositories, capsules, or in the liquid form, for example as solutions, suspensions or emulsions. Optionally, they contain moreover auxiliary materials, such as preservatives, stabilizers, wetting agents or emulsifiers, salts for altering osmotic pressure, or buffers.

Thus, the pharmacologically active compounds of this invention can be processed in accordance with conventional methods of galenic pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds, Suitable pharmaceutically acceptable carriers include but are not limited to water, salt solutions, alcohols, gum arabic, vegetable oils, benzyl alcohols, polyethylene glycols, gelatine carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

Generally, the compounds of this invention are dispensed in unit dosage form comprising 0.1 to 10 mg in a pharmaceutically acceptable carrier per unit dosage.

The dosage of the compounds according to this invention generally is 0.001 to 1 mg/kg/day, preferably 0.01 to 0.1, when administered to patients, e.g., humans to treat depression analogously to the known agent Idazoxan (BP 2068376).

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

PREPARATION OF STARTING COMPOUNDS 3-(13-Bromo-1-tert-butyldimethylsilyl-6-methyl-8α-ergolinyl)-1,1-diethylurea A solution of lithium diisopropylamide is made up from 400 ml of freshly distilled, anhydrous THF, 12.9 ml of anhydrous diisopropylamine, and 42.8 ml of n-butyllithium (in hexane) at 0° C. This solution is cooled to −20° C., combined with 8.21 g of 3-(13-bromo-6-methy8α-ergolinyl)-1,1-diethylurea (19.5 mmol), dissolved in 200 ml of freshly distilled, anhydrous THF at −20° C., and agitated for 15 minutes. At the same temperature, a solution of 10.7 g of tert-butyldimethylsilyl chloride in 150 ml of freshly distilled, anhydrous THF is added thereto, and the mixture is stirred again for 15 minutes. Then the batch is poured on ice, made alkaline with 25% strength ammonia, and extracted by shaking with methylene chloride. The mixture is chromatographed on silica gel with hexane, diisopropyl ether, methylene chloride, and methanol, and, after crystallization from ethyl acetate and diisopropyl ether, 7.3 g (70% of theory) of product is obtained.

$[\alpha]_D = -12°$ (0.5% in chloroform)

The following silyl compounds are produced analogously:

3-(13-bromo-1-tert-butyldimethylsilyl-6-n-propyl-8α-ergolinyl)-1,1-diethylurea 3-(12-bromo-1-tert-butyldimethylsilyl-6-methyl-8α-ergolinyl)-1,1-diethylurea $[\alpha]_D = +34°$ (0.5% in chloroform)

3-(12-bromo-1-tert-butyldimethylsilyl-9,10-didehydro6-methyl-8α-ergolinyl)-1,1-diethylurea 3-(13-bromo-1-tert-butyldimethylsilyl-2,3-dihydro-6-methyl-8α-ergolinyl)-1,1-diethylurea 3-(12-bromo-1-tert-butyldimethylsilyl-2,3-dihydro-6-methyl-8α-ergolinyl)-1,1-diethylurea

EXAMPLE 1

1,1-Diethyl-3-(6-methyl-13-methylthio-8α-ergolinyl)urea 3.2 ml (15 mmol) of distilled hexamethyldisilazane is combined under argon with 40 ml of anhydrous, freshly distilled toluene. After cooling this mixture to 0° C., 8.5 ml (14 mmol) of 15% strength n-butyllithium in hexane is added dropwise thereto and the mixture is stirred for 15 minutes at 0° C. Then a solution of 5.33 g of 3-(13-bromo-1-tert-butyldimethylsilyl-6-methyl-8α-ergolinyl)-1,1-diethylurea (10 mmol) in 200 ml of anhydrous, freshly distilled toluene is added thereto and the mixture is agitated for 15 minutes at 0° C. Thereafter 10 ml of distilled tetramethylethylenediamine is added thereto and the mixture cooled to −90° C. At this point in time, 50 ml of 1.4-molar tert-butyllithium (70 mmol) is added, and the mixture is agitated for 2 minutes.

To the solution of 13-lithium-ergolinylurea, a solution of 6.3 g of methanethiosulfonic acid S-methyl ester (10 mmol) in 50 ml of freshly distilled, anhydrous THF is added. After 10 minutes of agitation, the mixture is poured on ice, rendered alkaline with 25% strength ammonia solution, and extracted by shaking with methylene chloride.

The crude product is dissolved, to remove the silyl group, in 500 ml of methanol and stirred with 250 ml of 7N potassium hydroxide solution for 15 minutes at room temperature. The batch is again poured on ice and extracted by shaking with methylene chloride. After the solvent has been distilled off, the residue is chromatographed (yield: 1.27 g, 33% of theory) and crystallized from ethyl acetate and diisopropyl ether. Yield: 0.7 g (18% of theory).

$[\alpha]_D = -13°$ (0.25% in chloroform)

In a completely analogous fashion, the following compounds are produced with methanethiosulfonic acid S-methyl ester from the 12- and 13-bromoergolinylureas set forth below:

From 3-(12-bromo-1-tert-butyldimethylsilyl-6-methyl-8α-ergolinyl)-1,1-diethylurea:
1,1-diethyl-3-(6-methyl-12-methylthio-8α-ergolinyl)urea, yield 44% of theory, [α]$_D$=+24° (0.5% in chloroform).

From 3-(12-bromo-1-tert-butyldimethylsilyl-2,3-dihydro-6-methyl-8α-ergolinyl)-1,1-diethylurea:
1,1-diethyl-3-(2,3-dihydro-6-methyl-12-methylthio-8α-ergolinyl)urea, yield 80% of theory, [α]$_D$=+41.7° (0.5% in chloroform).

From 3-(13-bromo-1-tert-butyldimethylsilyl-2,3-dihydro-6-methyl-8α-ergolinyl)-1,1-diethylurea:
1,1-diethyl-3-(2,3-dihydro-6-methyl-13-methylthio-8α-ergolinyl)urea.

From 3-(12-bromo-1-tert-butyldimethylsilyl-9,10-didehydro-6-methyl-8α-ergolinyl)-1,1-diethylurea:
3-(9,10-didehydro-6-methyl-12-methylthio-8α-ergolinyl)-1,1-diethylurea.

From 3-(13-bromo-1-tert-butyldimethylsilyl-6-n-propyl-8α-ergolinyl)-1,1-diethylurea:
1,1-diethyl-3-(13-methylthio-6-n-propyl-8α-ergolinyl)urea.

From 3-(13-bromo-1-tert-butyldimethylsilyl-2,3-dihydro-6-n-propyl-8α-ergolinyl)-1,1-diethylurea:
1,1-diethyl-3-(2,3-dihydro-13-methylthio-6-n-propyl-8α-ergolinyl)urea.

By replacing methanethiosulfonic acid S-methyl ester by other electrophilic compounds, the following are analogously obtained:

With toluenethiosulfonic acid S-ethyl ester and 3-(12-bromo-1-tert-butyldimethylsilyl-6-methyl-8α-ergolinyl)-1,1-diethylurea:
1-diethyl-3-(12-ethylthio-6-methyl-8α-ergolinyl)urea, yield 48% of theory, [α]$_D$=+98° (0.5% in chloroform).

With toluenethiosulfonic acid S-n-propyl ester and 3-(13-bromo-1-tert-butyldimethylsilyl-6-methyl-8α-ergolintl)-1,1-diethylurea:
1-diethyl-3-(6-methyl-13-n-propylthio-8α-ergolinyl)urea.

With dibenzyl disulfide and 3-(13-bromo-1-tert-butyldimethylsilyl-6-methyl-8α-ergolinyl)-1,1-diethylurea:
3-(13-benzylthio-6-methyl-8α-ergolinyl)-1,1-diethylurea.

With diphenyl disulfide and 3-(13-bromo-1-tert-butyldimethylsilyl-6-methyl-8α-ergolinyl)-1,1-diethylurea:
1-diethyl-3-(6-methyl-13-phenylthio-8α-ergolinyl)urea.

With tetraisopropylthiuram disulfide and 3-(13-bromo-1-tert-butyldimethylsilyl-6-methyl-8α-ergolinyl)-1,1-diethylurea and hydrolysis with 20% ethanolic potassium hydroxide solution:
1-diethyl-3-(13-mercapto-6-methyl-8α-ergolinyl)urea.

With nitrobenzene and 3-(13-bromo-1-tert-buyldimethylsilyl-6-methyl-8α-ergolinyl)-1,1-diethylurea:
1,1-diethyl-3-(13-hydroxy-6-methyl-8α-ergolinyl)urea, yield 34% of theory, [α]$_D$=+11° (0.5% in methanol).

With boric acid trimethyl ester and 3-(12-bromo-1-tert-butyldimethylsilyl-2,3-dihydro-6-methyl-8α-ergolinyl)-1,1-diethylurea and subsequent treatment with hydrogen peroxide:
1,1-diethyl-3-(2,3-dihydro-12-hydroxy-6-methyl-8α-ergolinyl)urea.

With nitrobenzene and 3-(13-bromo-1-tert-butyldimethylsilyl-2,3-dihydro-6-methyl-8α-ergolinyl)-1,1-diethylurea:
1,1-diethyl-3-(2,3-dihydro-13-hydroxy-6-methyl-8α-ergolinyl)urea.

With nitrobenzene and 3-(12-bromo-1-tert-butyldimethylsilyl-9,10-didehydro-6-methyl-8α-ergolinyl)-1,1diethylurea:
3-(9,10-didehydro-12-hydroxy-6-methyl-8α-ergolinyl)-1,1-diethylurea, yield 31% of theory.

With nitrobenzene and 3-(13-bromo-1-tert-butyldimethylsilyl-6-n-propyl-8α-ergolinyl)-1,1-diethylurea:
1,1-diethyl-3-(13-hydroxy-6-n-propyl-8α-ergolinyl)urea.

With trimethylsilyl isocyanate and 3-(12-bromo-1-tert-butyldimethylsilyl-6-methyl-8α-ergolinyl)-1,1-diethylurea:
8α-(3,3-diethylureido)-6-methylergoline-12-carboxylic acid amide, yield 15% of theory.

With methyl isothiocyanate and 3-(13-bromo-1-tert-butyldimethylsilyl-6-methyl-8α-ergolinyl)-1,1-diethylurea:
8α-(3,3-diethylureido)-6-methylergoline-13-thiocarboxylic acid methylamide, yield 29% of theory, [α]$_D$=+32° (0.5% in chloroform).

With methyl isothiocyanate and 3-(13-bromo-1-tert-butyldimethylsilyl-2,3-dihydro-6-methyl-8α-ergolinyl)-1,1diethylurea:
8α-(3,3-diethylureido)-2,3-dihydro-6-methylergoline-13-thiocarboxylic acid methylamide.

With carbon dioxide and 3-(13-bromo-1-tert-butyldimethylsilyl-6-methyl-8α-ergolinyl)-1,1-diethylurea:
8α-(3,3-diethylureido)-6-methylergoline-13-carboxylic acid.

With methyl chloroformate and 3-(13-bromo-1-tert-butyldimethylsilyl-6-methyl-8α-ergolinyl)-1,1-diethylurea:
8α-(3,3-diethylureido)-6-methylergoline-13-carboxylic acid methyl ester.

With dimethylformamide and 3-(13-bromo-1-tert-butyldimethylsilyl-6-methyl-8α-ergolinyl)-1,1-diethylurea:
1,1-diethyl-3-(13-formyl-6-methyl-8α-ergolinyl)urea, yield 13%, [α]$_D$=−11° (0.5% in chloroform).

With benzaldehyde and 3-(13-bromo-1-tert-butyldimethylsilyl-6-methyl-8α-ergolinyl)-1,1-diethylurea:
1,1-diethyl-3-[6-methyl-13-(phenylhydroxymethyl)-8α-ergolinyl]urea.

With N,N-dimethylmethylemiminium iodide and 3-(13-bromo-1-tert-butyldimethylsilyl-6-methyl-8α-ergolinyl)-1,1-diethylurea:
1,1-diethyl-3-(13-dimethylaminomethyl-6-methyl-8α-ergolinyl)urea.

With N,N-dimethylmethyleniminium chloride and 3-(12-bromo-1-tert-butyldimethylsilyl-9,10-didehydro-6-methyl-8α-ergolinyl)-1,1-diethylurea:
3-(9,10-didehydro-12-dimethylaminomethyl-6-methyl-8α-ergolinyl)-1,1-diethylurea.

With methyl iodide and 3-(12-bromo-1-tert-butyldimethylsilyl-6-methyl-8α-ergolinyl)-1,1-diethylurea:
1,1-diethyl-3-(6,12-dimethyl-8α-ergolinyl)urea, yield 31%, [α]$_D$=+5.5° (0.5% in chloroform).

With methyl iodide and 3-(13-bromo-1-tert-butyldimethylsilyl-6-methyl-8α-ergolinyl)-1,1-diethylurea:
1,1-diethyl-3-(6,13-dimethyl-8α-ergolinyl)urea.

With isopropyl iodide and 3-(13-bromo-1-tert.-butyldimethylsilyl-2,3-dihydro-6-methyl-8α-ergolinyl)-1,1-diethylurea:
1,1-diethyl-3-(6-methyl-13-isopropyl-8α-ergolinyl)urea.

With isopropyl iodide and 3-(13-bromo-1-tert-butyldimethylsilyl-6-n-propyl-8α-ergolinyl)-1,1-diethylurea:
1,1-diethyl-3-(13-isopropyl-6-n-propyl-8α-ergolinyl)urea.

With trifluoroacetic anhydride and 3-(13-bromo-1-tert-butyldimethylsilyl-6-methyl-8α-ergolinyl)-1,1-diethylurea:
1,1-diethyl-3-(6-methyl-13-trifluoroacetyl-8α-ergolinyl)-urea.

With trifluoromethanesulfonic anhydride and 3-(13-bromo-1-tert-butyldimethylsilyl-6-methyl-8α-ergolinyl)-1,1-diethylurea:
[8α-(3,3-diethylureido)-6-methylergolin-13-yl](trifluoromethyl)sulfone.

With trimethylchlorosilane and 3-(13-bromo-1-tert-butyldimethylsilyl-6-methyl-8α-ergolinyl)-1,1-diethylurea:
1,1-diethyl-3-(6-methyl-13-trimethylsilyl-8α-ergolinyl)urea.

With acetyl chloride and 3-(13-bromo-1-tert-butyldimethylsilyl-6-methyl-8α-ergolinyl)-1,1-diethylurea:
3-(13-acetyl-6-methyl-8α-ergolinyl)-1,1-diethylurea.

With N-chlorosuccinimide and 3-(12-bromo-1-tert-butyldimethylsilyl-6-methyl-8α-ergolinyl)-1,1-diethylurea:
3-(12-chloro-6-methyl-8α-ergolinyl)-1,1-diethylurea.

With N-chlorosuccinimide and 3-(13-bromo-1-tert-butyldimethylsilyl-6-methyl-8α-ergolinyl)-1 1-diethylurea:
3-(13-chloro-6-methyl-8α-ergolinyl)-1,1-diethylurea.

With N-chlorosuccinimide and 3-(13-bromo-1-tert-butyldimethylsilyl-2,3-dihydro-6-methyl-8α-ergolinyl)-1,1-diethylurea:
3-(13-chloro-2,3-dihydro-6-methyl-8α-ergolinyl)-1,1-diethylurea.

With N-chlorosuccinimide and 3-(12-bromo-1-tert-butyldimethylsilyl-9,10-didehydro-6-methyl-8α-ergolinyl)1,1-diethylurea:
3-(12-chloro-9,10-didehydro-6-methyl-8α-ergolinyl)1,1-diethylurea.

With N-iodosuccinimide and 3-(12-bromo-1-tert-butyldimethylsilyl-6-methyl-8α-ergolinyl)-1,1-diethylurea:
1,1-diethyl-3-(12-iodo-6-methyl-8α-ergolinyl)urea.

With iodine and 3-(13-bromo-1-tert-butyldimethylsilyl-6-methyl-8α-ergolinyl)-1,1-diethylurea:
1,1-diethyl-3-(13-iodo-6-methyl-8α-ergolinyl)urea.

With N-iodosuccinimide and 3-(12-bromo-1-tert-butyldimethylsilyl-2,3-dihydro-6-methyl-8α-ergolinyl)-1,1diethylurea:
1,1-diethyl-3-(2,3-dihydro-12-iodo-6-methyl-8α-ergolinyl)urea.

With iodine and 3-(13-bromo-1-tert-butyldimethylsilyl2,3-dihydro-6-methyl-8α-ergolinyl)-1,1-diethylurea:
1,1-diethyl-3-(2,3-dihydro-13-iodo-6-methyl-8α-ergolinyl)urea.

With iodine and 3-(12-bromo-1-tert-butyldimethylsilyl9,10-didehydro-6-methyl-8α-ergolinyl)-1,1-diethylurea:
3-(9,10-didehydro-12-iodo-6-methyl-8α-ergolinyl)1,1-diethylurea.

With iodine and 3-(13-bromo-1-tert-butyldimethylsilyl-6-n-propyl-8α-ergolinyl)-1,1-diethylurea:
1,1-diethyl-3-(13-iodo-6-methyl-8α-ergolinyl)urea.

EXAMPLE 2

1,1-Diethyl-3-(13-hydroxy-6-methyl-8-α-ergolinyl)urea

Under argon, 419 mg of 3-(13-bromo-6-methyl-8α-ergolinyl)-1,1-diethylurea (1 mmol) is dissolved in 15 ml of anhydrous, freshly distilled THF, cooled to −20° C., and combined with 5 ml of a 1.4-molar solution of tert-butyllithium in hexane. The mixture is stirred for 2 hours at 0° C., cooled thereafter to −70° C., and combined with 0.5 g of nitrobenzene in 10 ml of anhydrous, freshly distilled THF. After 10 minutes of agitation, the mixture is poured on ice, made alkaline with 25% strength ammonia solution, and extracted by shaking with methylene chloride. The residue is purified by chromatography on silica gel and crystallized from ethyl acetate and diisopropyl ester. Yield: 131 mg (37% of theory), $[\alpha]_D = +11°$ (0.5% in methanol).

The following compounds are prepared analogously:
With nitrobenzene and 3-(12-bromo-9,10-didehydro-6-methyl8α-ergolinyl)-1,1-diethylurea:
1,1-diethyl-3-(9,10-didehydro-12-hydroxy-6-methyl-8α-ergolinyl)urea, yield 41%.

With methanethiosulfonic acid S-methyl ester and 3-(13-bromo-6-methyl-8α-ergolinyl)-1,1-diethylurea:
1,1-diethyl-3-(6-methyl-13-methylthio-8α-ergolinyl)urea in a 46% yield. $[\alpha]_D = -13°$ (0.25% in chloroform).

With methyl isothiocyanate and 3-(13-bromo-6-methyl-8α-ergolinyl)-1,1-diethylurea:
8α-(3,3-diethylureido)-6-methylergoline-13-thiocarboxylic acid amide in a 42% yield. $[\alpha]_D = +32°$ (0.5% in chloroform).

With dimethylformamide and 3-(12-bromo-6-methyl-8α-ergolinyl)-1,1-diethylurea:
1,1-diethyl-3-(12-formyl-6-methyl-8α-ergolinyl)urea in a 70% yield. $[\alpha]_D = +20.6°$ (0.5% in chloroform).

With dimethylformamide and 3-(12-bromo-2,3-dihydro-6-methyl-8α-ergolinyl)-1,1-diethylurea:
1,1-diethyl-3-(12-formyl-2,3-dihydro-6-methyl-8α-ergolinyl)urea in a 65% yield. $[\alpha]_D = +14°$ (0.5% in chloroform).

With dimethylacetamide and 3-(12-bromo-6-methyl-8α-ergolinyl)-1,1-diethylurea:
3-(12-acetyl-6-methyl-8α-ergolinyl)-1,1-diethylurea in a 23% yield. $[\alpha]_D = +57.5°$ (0.5% in chloroform).

With dimethyl carbonate and 3-(12-bromo-6-methyl-8α-ergolinyl)-1,1-diethylurea:
8α-(3,3-diethylureido)-6-methylergoline-12-carboxylic acid methyl ester in a 47% yield. $[\alpha]_D = +72°$ (0.5% in chloroform).

With carbon dioxide and 3-(12-bromo-6-methyl-8α-ergolinyl)-1,1-diethylurea:
8α-(3,3-diethylureido)-6-methylergoline-12-carboxylic acid in a 40% yield.

With trifluoroacetic anhydride and 3-(12-bromo-6-methyl-8α-ergolinyl)-1,1-diethylurea:
1,1-diethyl-3-(6-methyl-12-trifluoroacetyl-8α-ergolinyl)-urea in a 19% yield. $[\alpha]_D = +6$ (0.25% in chloroform).

EXAMPLE 3

1,1-Diethyl-3-(6-methyl-13-methylsulfinyl-8α-ergolinyl)urea 210 mg of 1,1-diethyl-3-(6-methyl-13-methylthio8α-ergolinyl)urea is dissolved in 20 ml of acetonitrile, and sodium metaperiodate, dissolved in 5 ml of water, is added in portions to this solution. The latter is stirred for 16 hours at 50° C., the residue is divided between methylene chloride and water, the organic phase is dried with sodium sulfate, and evaporated. The residue is chromatographed on silica gel.

The following compounds are prepared in analogy thereto:
With sodium metaperiodate and 1,1-diethyl-3-(6-methyl-12-methylthio-8α-ergolinyl)urea:

1,1-diethyl-3-(6-methyl-12-methylsulfinyl-8α-ergolinyl)-urea, yield 48% of theory. $[α]_D= +28.8$ (0.5% in chloroform).

EXAMPLE 4

3-(13-Acetoxy-6-methyl-8α-ergolinyl)-1,1-diethylurea

At room temperature, 100 mg of 1,1-diethyl-3-(13-hydroxy-6-methyl-8α-ergolinyl)urea is dissolved in 1 ml of pyridine and 1 ml of acetic anhydride. After one hour, the mixture is poured on ice, extracted, after 15 minutes of stirring, with methylene-chloride, the organic phase is dried with sodium sulfate, and evaporated. The residue is crystallized from ethyl acetate.

EXAMPLE 5

3-(12-Cyano-6-methyl-8α-ergolinyl)-1,1-diethylurea 383 mg of [8α-(3,3-diethylureido)-6-methylergolin-12-yl]carboxylic acid amide (1 mmol) is dissolved in 25 ml of chloroform, 3 ml of phosphorus oxychloride is added thereto, and the mixture is agitated for 16 hours at 55° C. The mixture is poured on ice, allowed to stand for 30 minutes, then made alkaline with 1N potassium hydroxide solution, and extracted with methylene chloride. The organic phase is dried with sodium sulfate and evaporated. The residue is crystallized from ethyl acetate in a 43% yield. $[α]_D= +16°$ (0.5% in chloroform).

EXAMPLE 6

1,1-Diethyl-3-(6-methyl-13-hydroxymethyl-8α-ergolinyl)urea 80 mg of lithium aluminum hydride (2 mmol) is suspended in 5 ml of anhydrous, freshly distilled THF and, at room temperature, a solution of 350 mg of 1,1-diethyl-3-(13-formyl-6-methyl-8α-ergolinyl)urea (1 mmol), dissolved in 10 ml of anhydrous, freshly distilled THF, is added thereto. After one hour of stirring at room temperature, the mixture is combined under cooling with 5 ml of 1N hydrochloric acid, 5 ml of 2N tartaric acid solution is added, and the mixture is rendered alkaline with aqueous ammonia, extracted with ethyl acetate, the organic phase dried and evaporated. After chromatography on silica gel, the compound is crystallized from ethyl acetate.

The following compounds are prepared analogously:
With lithium aluminum hydride and 1,1-diethyl-3-(12-formyl-6-methyl-8α-ergolinyl)urea:
1,1-diethyl-3-(12-hydroxymethyl-6-methyl-8α-ergolinyl)urea in a 51% yield. $[α]_D= +47°$ (0.5% in chloroform).
With lithium aluminum hydride and 1,1-diethyl-3-(2,3-dihydro-12-formyl-6-methyl-8α-ergolinyl)urea:
1,1-diethyl-3-(2,3-dihydro-12-hydroxymethyl-8α-ergolinyl)urea as the hydrogen fumarate in a 33% yield.
$[α]_D= -3.2°$ (0.5% in methanol).

EXAMPLE 7

1,1-Diethyl-3-(12-hydroxy-6-methyl-8α-ergolinyl)urea

Under an argon atmosphere, a solution of 67 mg of diisopropylamine in 0.5 ml of absolute tetrahydrofuran is combined under agitation at 0°-5° C. with 0.42 ml of n-butyllithium (15% strength in hexane); the mixture is cooled to -20° C., a solution of 305 mg of 3-(12-bromo-1-tert-butyldimethylsilyl-6-methyl-8α-ergolinyl)-1,1diethylurea in 2.5 ml of absolute tetrahydrofuran is added dropwise thereto, and the mixture is stirred for 30 minutes at this temperature. The mixture is cooled to -70° C., 3 ml of tert-butyllithium (2.3-molar in pentane) is added dropwise thereto, and the mixture is stirred at this temperature for 30 minutes. Then, at -70° C., 0.62ml of boric acid trimethyl ester is added, the mixture is agitated at this temperature for 15 minutes and at room temperature for 2 hours, cooled to -10° C., combined in succession with 0.13 ml of glacial acetic acid, a mixture of 0.34 ml of 30% strength hydrogen peroxide and 0.34 ml of water, and stirred for 20 minutes at 0° C.

The reaction mixture is poured on ice, made alkaline with 25% strength ammonia solution, and extracted with dichloromethane. The combined organic phases are washed with a 10% ammonium iron sulfate solution, dried with magnesium sulfate, and concentrated. The resultant product is dissolved in 1 ml of trifluoroacetic acid, stirred for 3 hours at +5° C., the reaction mixture is poured on ice, rendered alkaline with 25% strength ammonia solution, and extracted with dichloromethane.

The combined organic phases are dried over magnesium sulfate, concentrated, and the crude product is chromatographed on silica gel with dichloromethane/methanol/25% strength ammonia solution in a proportion of 98:2:0.1, thus obtaining 50 mg of 1,1-diethyl-3-(12-hydroxy-6-methyl-8α-ergolinyl)urea.

$[α]_D= +18.4°$ (0.5% in chloroform).

EXAMPLE 8

1,1-Diethyl-3-(6-methyl-12-methylthio-8α-ergolinyl)-thiourea

At -20° C., 5.79 g of 1,1-diethyl-3-(6-methyl-12-methylthio-8α-ergolinyl)urea (15 mmol) is dissolved in a mixture of 4.13 g of freshly distilled phosphorus oxychloride (45 mmol) and 50 ml of anhydrous methylene chloride and the temperature is allowed to rise within 4 hours to +10° C. The mixture is stirred overnight at room temperature and then another 2 hours at 40° C., and the solvent is subsequently distilled off under vacuum. The residue is dissolved in 50 ml of anhydrous acetonitrile, cooled to -10° C., combined with 7.2 g of potassium ethylxanthate (45 mmol), and stirred at room temperature for 20 hours. The solvent is exhaustively removed by distillation; then the mixture is distributed between ethyl acetate and saturated sodium carbonate solution; the organic phase is dried with sodium sulfate and evaporated. The residue is crystallized from ethyl acetate, yielding 82%.

$[α]_D= +48°$ (0.5% in chloroform).

The following thioureas are analogously produced from the corresponding ureas:
1,1-diethyl-3-(6-methyl-13-methylthio-8α-ergolinyl)thiourea
8α-(3,3-diethylthioureido)-6-methylergoline-13thiocarboxylic acid methylamide
1,1-diethyl-3-(2,3-dihydro-6-methyl-13-methylthio-8α-ergolinyl)thiourea
3-(9,10-didehydro-6-methyl-12-methylthio-8α-ergolinyl)-1,1-diethylthiourea
1,1-diethyl-3-(13-methylthio-6-n-propyl-8α-ergolinyl)-thiourea

EXAMPLE 9

3-(12-Cyano-2,3-dihydro-6-methyl-8α-ergolinyl)-1,1-diethylurea

A suspension of 500 mg of 1,1-diethyl-3-(2,3-dihydro-12-formyl-6-methyl-8α-ergolinyl)urea and 460 mg of hydroxylamine-O-sulfonic acid in 5 ml of water is stirred for 20 hours at room temperature. The reaction mixture is poured on ice, set to be alkaline with 25% strength ammonia solution, and extracted with dichloromethane. The organic phase is dried (Na$_2$SO$_4$), concentrated, the residue chromatographed on silica gel with dichloromethane/methanol=95/5 as the eluting agent, and crystallized from ethyl acetate/pentane. Yield 26% of theory.

[α]$_D$= +26° (0.5% in chloroform).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 12- or 13-substituted ergoline of the formula

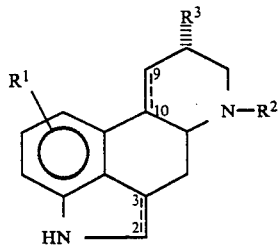

wherein
R$^1$ is in the 12- or 13- position and is OR', SH, SR$^5$, SOR$^5$, C(=X)R$^6$, —CR$^8$R$^9$R$^{10}$, —SO$_2$CF$_3$, Si(CH$_3$)$_3$, CN, Cl or I,
R' is H, lower alkyl or C$_{1-5}$ alkanoyl,
R$^5$ is lower alkyl, C$_{6-10}$-aryl, or C$_{6-10}$-aryl C$_{1-6}$-alkyl
X is O or S,
R$^6$ is H, CF$_3$, C$_{6-10}$ aryl, lower alkyl, amino, amino mono or disubstituted by lower alkyl, or OR$^7$,
R$^7$ is hydrogen or lower alkyl,
R$^8$ is H, OH, O-C$_{1-5}$-alkanoyl, O-lower alkyl, C$_{6-10}$-aryl, lower alkyl, amino, or amino substituted by lower alkyl,
R$^9$ and R$^{10}$ are identical or different and each is H, lower alkyl or C$_{6-10}$-aryl,
R$^2$ is lower alkyl
R$^3$ is NH-CO-NEt$_2$ or NH-CS-NEt$_2$,
C$_9$C$_{10}$ and C$_2$C$_3$ each independently is a CC-single or a C=C-double bond, and
the hydrogen atom in the 10-position is in the alpha-configuration if C$_9$C$_{10}$ is a CC-single bond, and the hydrogen atom in the 3-position is in the alpha- or beta-configuration if C$_2$C$_3$ is a CC-single bond,
or a pharmaceutically acceptable acid addition salt thereof.

2. A compound of claim 1, wherein R$^1$ is in the 12-position.

3. A compound of claim 1, wherein R$^1$ is in the 13-position.

4. A compound of claim 1, wherein R$^1$ is OR'.

5. A compound of claim 1, wherein R$^1$ is SH, SR$^5$ or SOR$^5$.

6. A compound of claim 1, wherein R$^1$ is C(=X)R$^6$.

7. A compound of claim 1, wherein R$^1$ is CR$^8$R$^9$R$^{10}$.

8. A compound of claim 1, wherein R$^1$ is SO$_2$CF$_3$.

9. A compound of claim 1, wherein R$^1$ is Si(CH$_3$)$_3$.

10. A compound of claim 1, wherein R$^1$ is CN, Cl or I.

11. A compound of claim 1, wherein R$^3$ is NHCONEt$_2$.

12. A compound of claim 1, wherein R$^3$ is NHCSNEt$_2$.

13. 1,1-Diethyl-3-(6-methyl-13-methylthio-8α-ergolinyl)urea,
1,1-diethyl-3-(6-methyl-12-methylthio-8α-ergolinyl)urea,
1,1-diethyl-3-(2,3-dihydro-6-methyl-12-methylthio-8α-ergolinyl)urea,
3-(9,10-didehydro-6-methyl-12-methylthio-8α-ergolinyl)-1,1-diethylurea,
1,1-diethyl-3-(13-methylthio-6-n-propyl-8α-ergolinyl)urea,
1,1-diethyl-3-(2,3-dihydro-13-methylthio-6-n-propyl-8α-ergolinyl)urea,
1,1-diethyl-3-(12-ethylthio-6-methyl-8α-ergolinyl)urea,
1,1-diethyl-3-(6-methyl-13-phenylthio-8α-ergolinyl)urea,
1,1-diethyl-3-(2,3-dihydro-12-hydroxy-6-methyl-8α-ergolinyl)urea,
1,1-diethyl-3-(2,3-dihydro-13-hydroxy-6-methyl-8α-ergolinyl)urea,
3-(9,10-didehydro-12-hydroxy-6-methyl-8α-ergolinyl)-1,1-diethylurea,
1,1-diethyl-3-(13-hydroxy-6-n-propyl-8α-ergolinyl)urea, 8α-(3,3-diethylureido)-6-methylergoline-12-carboxylic acid amide,
8α-(3,3-diethylureido)-6-methylergoline-13-thiocarboxylic acid methylamide,
1,1-diethyl-3-(13-formyl-6-methyl-8α-ergolinyl)urea,
1,1-diethyl-3-(13-dimethylaminomethyl-6-methyl-8α-ergolinyl)urea,
1,1-diethyl-3-(6,13-dimethyl-8α-ergolinyl)urea,
1,1-diethyl-3-(6-methyl-13-isopropyl-8α-ergolinyl)urea
3-(13-acetyl-6-methyl-8α-ergolinyl)-1,1-diethylurea,
3-(13-chloro-6-methyl-8α-ergolinyl)-1,1-diethylurea,
3-(13-chloro-2,3-dihydro-6-methyl-8α-ergolinyl)-1,1-diethylurea,
1,1-diethyl-3-(13-iodo-6-methyl-8α-ergolinyl)urea,
1,1-diethyl-3-(2,3-dihydro-12-iodo-6-methyl-8α-ergolinyl)urea,
1,1-diethyl-3-(2,3-dihydro-13-iodo-6-methyl-8α-ergolinyl)urea,
1,1-diethyl-3-(13-hydroxy-6-methyl-8α-ergolinyl)urea,
1,1-diethyl-3-(9,10-didehydro-12-hydroxy-6-methyl-8α-ergolinyl)urea,
1,1-diethyl-3-(6-methyl-13-methylthio-8α-ergolinyl)urea,
8α-(3,3-diethylureido)-6-methylergolinyl-13-thiocarboxylic acid methylamide,
3-(13-acetoxy-6-methyl-8α-ergolinyl)-1,1-diethylurea,
3-(12-cyano-6-methyl-8α-ergolinyl)-1,1-diethylurea,
1,1-diethyl-3-(6-methyl-13-hydroxymethyl-8α-ergolinyl)urea,
1,1-diethyl-3-(12-hydroxy-6-methyl-8α-ergolinyl)urea,
1,1-diethyl-3-(6-methyl-12-methylthio-8α-ergolinyl)-thiourea,
1,1-diethyl-3-(6-methyl-13-methylthio-8α-ergolinyl)-thiourea, 8α-(3,3-diethylthioureido)-6-methylergoline-13thiocarboxylic acid methylamide, 1,1-diethyl-3-(2,3-dihydro-6-methyl-13-methylthio-8α-ergolinyl)thiourea, 3-(9,10-didehydro-6-methyl-12-methylthio-8α-ergolinyl)-1,1-diethylthiourea, 1,1-diethyl-3-(13-methylthio-6-n-propyl-8α-ergolinyl)-thiourea.

14. A pharmaceutical composition comprising an effective amount of a compound of claim 1 and a pharmaceutically acceptable carrier.

15. A composition of claim 14 wherein the amount of said compound is 0.1–10 mg.

16. A method of treating the schizophrenic array of symptoms comprising administering a compound of claim 1.

17. A method of treating depression comprising administering a compound of claim 1.

18. A method of treating hypertension comprising administering a compound of claim 1.

19. A method of blocking central alpha$_2$-receptors comprising administering a compound of claim 1.

* * * * *

UNITED STATES PATENT AND TRADEMARK OFFICE
CERTIFICATE OF CORRECTION

PATENT NO. : 4,863,929                                        Page 1 of 2

DATED : September 5, 1989

INVENTOR(S) : SAUER ET AL

It is certified that error appears in the above-identified patent and that said Letters Patent is hereby corrected as shown below:

Column 15, claim 1, line 36:

reads "$C(=X)R^6, -CR^8R^9R^{10}, -SO_2CF_3, Si(CH_3)_3, CN,$"

should read --$C(=X)R^6, -CR^8R^9R^{10}, -SO_2CF_3, -Si(CH_3)_3, CN,$ --

Column 15, claim 1, line 39:

reads "$R^5$ is lower alkyl, $C_{6-10}$-aryl, or $C_{6-10}$-aryl $C_{1-6}$-alkyl"

should read -- $R^5$ is lower alkyl, $C_{6-10}$-aryl, or $C_{6-10}$-aryl-$C_{1-6}$-alkyl --

Column 15, claim 1, line 51:

reads "$C_9C_{10}$ and $C_2C_3$ each independently is a CC-single or"

should read -- $C_9\text{---}C_{10}$ and $C_2\text{---}C_3$ each independently is a CC-single or"

Column 15, claim 1, line 54:

reads "configuration if $C_9C_{10}$ is a CC-single bond, and the"

should read -- configuration if $C_9\text{---}C_{10}$ is a CC-single bond, and the --

UNITED STATES PATENT AND TRADEMARK OFFICE
CERTIFICATE OF CORRECTION

PATENT NO. : 4,863,929

DATED : September 5, 1989

INVENTOR(S) : SAUER ET AL

It is certified that error appears in the above-identified patent and that said Letters Patent is hereby corrected as shown below:

Column 15, claim 1, line 56:

reads "beta-configuration if $C_2C_3$ is a CC-single bond,"

should read -- beta-configuration if $C_2\text{---}C_3$ is a CC-single bond, --

Signed and Sealed this

Seventh Day of August, 1990

Attest:

HARRY F. MANBECK, JR.

*Attesting Officer*     *Commissioner of Patents and Trademarks*